US011786212B1

(12) United States Patent
Šablauskas et al.

(10) Patent No.: US 11,786,212 B1
(45) Date of Patent: Oct. 17, 2023

(54) ECHOCARDIOGRAM CLASSIFICATION WITH MACHINE LEARNING

(71) Applicant: UAB Ligence, Vilnius (LT)

(72) Inventors: Karolis Šablauskas, Vilnius (LT); Arnas Karužas, Vilnius (LT); Ieva Kažukauskienė, Vilnius (LT); Antanas Kiziela, Vilnius (LT)

(73) Assignee: UAB Ligence, Vilnius (LT)

( * ) Notice: Subject to any disclaimer, the term of this patent is extended or adjusted under 35 U.S.C. 154(b) by 0 days.

(21) Appl. No.: 18/081,886

(22) Filed: Dec. 15, 2022

(51) Int. Cl.
| | |
|---|---|
| *A61B 8/00* | (2006.01) |
| *A61B 8/08* | (2006.01) |
| *G16H 50/20* | (2018.01) |
| *G16H 30/20* | (2018.01) |
| *G06V 10/56* | (2022.01) |
| *G06V 10/82* | (2022.01) |
| *G06T 7/00* | (2017.01) |

(52) U.S. Cl.
CPC .......... *A61B 8/0883* (2013.01); *G06T 7/0012* (2013.01); *G06V 10/56* (2022.01); *G06V 10/82* (2022.01); *G16H 30/20* (2018.01); *G16H 50/20* (2018.01); *G06T 2207/10132* (2013.01); *G06T 2207/30048* (2013.01)

(58) Field of Classification Search
CPC ...... A61B 8/0883; G16H 30/20; G16H 50/20; G06V 10/56; G06T 7/0012; G06T 2207/10132; G06T 2207/30048
See application file for complete search history.

(56) References Cited

U.S. PATENT DOCUMENTS

| | | | |
|---|---|---|---|
| 2002/0151794 A1* | 10/2002 | Li | A61B 8/065 600/454 |
| 2022/0130046 A1* | 4/2022 | Schreckenberg | G06V 10/25 |
| 2023/0009891 A1* | 1/2023 | Wei | A61B 8/5223 |

FOREIGN PATENT DOCUMENTS

WO    2020121014 A1    6/2020

OTHER PUBLICATIONS

Akkus et al., "A Survey of Deep-Learning Applications in Ultrasound: Artificial Intelligence-Powered Ultrasound for Improving Clinical Workflow", Sep. 2019, Journal of the American College of Radiology, vol. 16, Issue 9, Part B, pp. 1318-1328.

(Continued)

*Primary Examiner* — Joel F Brutus (57) ABSTRACT

A method for analysing a structure within a patient's heart includes receiving a patient study including a plurality of images of the patient's heart obtained by an ultrasound device, extracting respective sets of pixel data from the images, and using trained machine learning algorithms to analyse the sets of pixel data to a) identify first images captured using a colour Doppler modality and assign the first images to said structure, b) identify second images captured using spectral Doppler modality and assign the second images to said structure, c) determine a flow convergence zone radius from an analysis of the first images; and d) determine a maximum gradient of structure, from an analysis of the second images. The flow convergence zone radius, the maximum gradient of structure, and a Nyquist value identified for the colour Doppler modality, are combined to determine an Effective Regurgitant Orifice Area for the structure.

11 Claims, 4 Drawing Sheets

(56) References Cited

OTHER PUBLICATIONS

Siemens ACUSON SC2000™ ultrasound system PRIME™, retrieved on Jun. 12, 2023, from URL: https://www.siemens-healthineers.com/ultrasound/news-and-innovations/advancing-3d-tee, 6 pages.

Van Sloun et al., "Deep learning in Ultrasound Imaging", Published 2020 Computer Science, Engineering Proceedings of the IEEE, Jul. 2019, arXiv:1907.02994v2, 19 pages.

Son et al., "Automated Quantification of Mitral Regurgitation by Three Dimensional Real Time Full Volume Color Doppler Transthoracic Echocardiography: A Validation with Cardiac Magnetic Resonance Imaging and Comparison with Two Dimensional Quantitative Methods" Jun. 2013, Journal of Cardiovascular Ultrasound, vol. 21, No. 2, pp. 81-90.

Wang et al., "Auto-weighting for Breast Cancer Classification in Multimodal Ultrasound", Aug. 2020, arXiv:2008.03435v1, 10 pages.

Yang et al., "Self-supervised learning assisted diagnosis for mitral regurgitation severity classification based on color Doppler echocardiography", Annals of Translation Medicine, Jan. 2022, vol. 10, No. 1, 14 pages.

Zoghbi et al., " Recommendations for Noninvasive Evaluation of Native Valvular Regurgitation: A Report from the American Society of Echocardiography Developed in Collaboration with the Society for Cardiovascular Magnetic Resonance", ASE Guidelines and Standards, Journal of American Society of Echocardiography, Apr. 2017, vol. 30, No. 4, pp. 303-371.

\* cited by examiner

ECHOCARDIOGRAM CLASSIFICATION WITH MACHINE LEARNING

TECHNICAL FIELD

The present invention relates to echocardiogram classification with machine learning.

BACKGROUND

Valvular heart diseases are a subset of cardiovascular diseases and include any cardiovascular disease process involving one or more of the four valves of the heart (aortic, mitral, tricuspid and pulmonary). Valvular heart diseases are often related to ageing but may also be the result of congenital abnormalities or specific disease or physiologic processes including rheumatic heart disease and pregnancy.

Echocardiography is an important diagnostic aid in the morphological and functional assessment of valvular heart disease. Usually, in a patient echocardiogram examination (echoscopy examination), a clinician or ultrasound technician positions an ultrasonic scanning device onto a patient's chest area to capture a number of 2D-images of the patients' heart. The device emits sound waves into the chest such that reflected sound waves reveal details of the inner structure of the heart and the velocities of blood flows within it. The position of the ultrasound probe on the chest, and its angle relative to the chest, is varied during echoscopy examination in order to capture different anatomical sections as 2D-slices of the heart from different viewpoints.

The clinician or technician typically has options to supplement the 2D-images (hereinafter the brightness mode or "B-mode" images) with data captured from one or more other modalities. These modalities include continuous wave Doppler, pulsed wave Doppler and M-mode. Continuous wave Doppler and pulsed wave Doppler (hereinafter "spectral Doppler") visualise blood flow velocity during a time interval and perform a similar function in heart valvular disease evaluation. Information gained from the B-mode image can be further enhanced by visualising the blood flow direction using Doppler imaging (hereinafter "colour-Doppler"). A specific setting of the pulsed wave Doppler called "tissue wave echocardiography" allows capture of the velocity of the heart muscle (myocardium).

Typically, the supplemented B-mode images and other modality data are exported in files of DICOM™ format. [DICOM (Digital Imaging and Communications in Medicine) is an international standard to transmit, store, retrieve, print, process, and display medical imaging information.]

Whilst the type of modality (used to supplement the B-mode images) is partially indicated in the metadata associated with the DICOM file, the ultrasound device position, which dictates the cardiac structure that has been imaged, remains undetermined in the DICOM file immediately after capture of the images.

After a patient examination, a clinician/technician displays and reviews the images produced from the DICOM files, for example viewing a 2D image side-by-side with a colour Doppler image, manually labels and performs annotation of heart structures or functional artefacts, for example the left ventricular endocardial border (LV) or S' peak in tissue wave Doppler modality images, and takes measurements of them. This process relies on the operator's training and experience to recognize the view of the heart in each image, and their ability to identify landmark features and make the appropriate measurements. In a subsequent review of the image, a cardiologist displays and views the now labelled and annotated DICOM files, and previously recorded measurements, compares them to guideline values, and makes a diagnosis based on his or her interpretation. Of particular interest are the so-called Effective Regurgitant Orifice Area (EROA) and the Regurgitant Volume which are metrics used in the quantitative analysis of valvular insufficiency.

This substantially manual workflow process for analysing DICOM files requires a high degree of expertise, typically requiring input from a highly experienced cardiologist, is time-consuming, error-prone and inevitably gives rise to wide variations in interpretations between different operators. Partial automation may help to improve the process to some extent but the most efficient solution would be a fully automated one.

Solutions proposed for automated cardiac image interpretation to enable low cost assessment of cardiac function by non-experts are discussed, for example, in Z. Akkus et al., "A Survey of Deep-Learning Applications in Ultrasound: Artificial Intelligence-Powered Ultrasound for Improving Clinical Workflow", September 2019, Journal of the American College of Radiology 16(9):1318-1328, DOI: 10.1016/j.jacr.2019.06.004. Akkus considers recent technological advances in echocardiography, including colour-doppler, convolutional neural networks (CNN) and deep learning (DL). Akkus notes that:

"current Deep Learning models for ultrasound diagnosis use only 2-D cross-sectional images for making predictions. However, the information in 2-D cross-sections is limited and does not represent lesions completely. DL models trained on 3-D ultrasound data, ultrasound cine clips with multiple views of lesions, or spatiotemporal data could potentially improve the diagnostic accuracy of models and consider complete lesions. Furthermore, developing DL models that are trained on multimodal (B-mode, Doppler, contrast-enhanced ultrasound, and SWE) images, which provide complementary information to one another, could also improve the diagnostic accuracy of DL models."

R. J. G. van Sloun et al., "Deep learning in Ultrasound Imaging", Published 2020 Computer Science, Engineering Proceedings of the IEEE, describes colour-doppler it neural network, and FIG. 4. (a) depicts tissue doppler processing using a deep encoder-decoder network for an illustrative cardiac ultrasound application, displaying the wall between the right atrium and the aorta. FIG. 4(b) depicts a deep network architecture designed to encode input IQ data into a compressed latent space via a series of convolutional layers and spatial (max) pooling operations, while maintaining the functionality and performance of a typical Doppler processor (Kasai autocorrelator) using full uncompressed IQ data. FIG. 4(c) illustrates convergence of the network parameters during training, showing the relative root-mean-squared-errors (RMSE) on a test dataset for four data compression factors.

J. Wang et al., "Auto-weighting for Breast Cancer Classification in Multimodal Ultrasound", 8 Aug. 2020, describes colour-doppler as an ultrasound imaging modality and a neural network used to automate weight balancing among several different ultrasound modalities (B-mode, Doppler, SE, SWE). This method does not however mention classification of different cardiac views and object segmentation in the classified frames, and also does not mention segmentation of Doppler modality images.

WO2020121014A describes an automated workflow that is performed by software executing on at least one processor includes receiving a plurality of echocardiogram images taken by an ultrasound device. A filter separates the plurality of echocardiogram images into 2D-images and Doppler modality images based on an analysis of image metadata. The 2D-images and Doppler modality images are classified by view type. The cardiac chambers are segmented in the 2D-images, and the Doppler modality images are segmented to generate waveform traces, producing segmented 2D-images and segmented Doppler modality images. Using both sets of images, measurements of cardiac features for both left and right sides of the heart are obtained. The measurements are compared with international cardiac guidelines to generate conclusions and a report is output showing the calculated measurements that fall both within and outside of the guidelines.

The following publications provide further useful background information:

https://atm.amegroups.com/article/view/85237/html

F. Yang et al., "Self-supervised learning assisted diagnosis for mitral regurgitation severity classification based on color Doppler echocardiography" January 2022, describes a diagnostic system to assist physicians in grading MR severity based on colour video Doppler echocardiography via a self-supervised learning algorithm. The proposed method segments the mitral regurgitation jet.

J W. Son et al., "Automated Quantification of Mitral Regurgitation by Three Dimensional Real Time Full Volume Color Doppler Transthoracic Echocardiography: A Validation with Cardiac Magnetic Resonance Imaging and Comparison with Two Dimensional Quantitative Methods" June 2013, describes an automated method for grading severity of mitral regurgitation. However, the method can only be implemented in the three-dimensional (3D) full volume colour Doppler echocardiography and not the routinely performed two-dimensional echocardiography.

https://www.siemens-healthineers.com/ultrasound/news-and-innovations/advancing-3d-tee Siemens ACUSON SC2000™ ultrasound system PRIME™ platform has automated mitral regurgitation analysis capabilities using three-dimensional (3D) volume colour Doppler echocardiography.

Current American Society of Echocardiography (ASE) guidelines "Recommendations for Noninvasive Evaluation of Native Valvular Regurgitation: A Report from the American Society of Echocardiography Developed in Collaboration with the Society for Cardiovascular Magnetic Resonance" recommend using flow convergence to measure EROA and regurgitant volume.

SUMMARY

According to a first aspect of the present invention there is provided a computer-implemented method for analysing a structure within a patient's heart performed by a software component executing on at least one processor. The method comprises the steps of:

receiving from a memory, a patient study comprising a plurality of transthoracic echocardiography and/or transesophageal echocardiography images of a patient's heart obtained by an ultrasound device; and extracting respective sets of pixel data from the images.

One or more trained machine learning algorithms are then used to analyse the sets of pixel data to a) identify images captured using a colour Doppler modality and assign one or more of these images to said structure, b) identify images captured using spectral Doppler modality and assign one or more of these images to said structure, c) determine a flow convergence zone radius R from an analysis of the colour Doppler modality images assigned to the structure;

d) determine a maximum gradient of structure, PVreg, from an analysis of the spectral Doppler modality images assigned to the structure.

The flow convergence zone radius, R, the maximum gradient of structure PVreg, and a Nyquist value Va identified for the colour Doppler modality, are combined to determine an Effective Regurgitant Orifice Area, EROA for the structure.

The EROA for the structure may be determined according to the formula:

$$(2 * \pi * R^{**}2 \times Va)/\text{PVreg}.$$

The method may comprise using said one or more trained neural networks to determine a velocity time integral regurgitation, VTIreg, from an analysis of the spectral Doppler modality images assigned to the structure, the method further comprising combining the EROA and the VTIreg to determine a Regurgitant Volume for the structure.

The Regurgitant Volume may be determined using the formula:

$$\text{EROA} * \text{VTIreg}.$$

The method may comprise using one or more trained machine learning algorithms to locate said Nyquist value within the colour Doppler modality images assigned to the structure, and applying optical character recognition to the location to determine the Nyquist value.

The images may be cines and each cine comprises a plurality of frames.

For one or each of steps a) and b), said assignment of one or more of the images to said structure may comprise using a trained classification neural network to separately analyse a plurality of frames of the image for the presence of the structure and combining the outputs for the analysed frames to allocate the image to a structure.

For one or each of steps c) and d), a segmentation and landmark detection neural network may be used to identify a single frame of the images associated with the structure and having the largest flow convergence zone radius R and/or maximum gradient of structure, PVreg.

The images may be still images.

Each image may be received from said memory as a DICOM format file.

The structure that is analysed may be one of an aortic valve, mitral valve, pulmonary valve, tricuspid valve, interventricular septum, and interatrial septum.

According to a second aspect of the present invention there is provided a method of diagnosing cardiovascular disease and comprising performing the method of the above first aspect to determine an Effective Regurgitant Orifice Area, EROA for a structure of a heart.

DETAILED DESCRIPTION

During transthoracic echocardiogram (TTE) examination, a patient is asked to remove any clothing covering the upper half of their body and lay down on a bed. The sonographer or clinician performing the TTE applies lubricating gel to the ultrasound probe which is attached to a nearby ultrasound machine or connected wirelessly to a handheld device (e.g. mobile phone or tablet). The ultrasound machine or handheld device displays and records the images produced. The ultrasound probe is moved across the patient's chest which allows observing and focusing on different parts of the patient's heart. Imaging modes can be changed to visualise different features of the blood flow or the heart. B-mode is normally used for quantifying chamber and other heart structure size, whereas spectral Doppler and colour Doppler imaging modes are used for visualising blood flow. Video feed in the ultrasound machine or handheld device can be stopped to allow measurement of a specific feature. The clinician or sonographer follows a protocol and obtains a list of heart parameters. Finally, the obtained images can be saved in a DICOM format and further exported to, e.g. a hospital picture archival and communications system.

A computer implemented method of analysing images obtained using echocardiography will now be described, as well as a process of determining the Effective Regurgitant Orifice Area (EROA) and the Regurgitant Volume for patient from whom the images were obtained. These images may be still images or video clips, referred to hereinafter as "cine images" or merely "cines". The images, still or cine, may also be referred to as "echocardiograms". The images may have been obtained using any suitable echocardiography system, although an exemplary system include GE Healthcare Vivid S70, Philips Medical Systems EPIQ CVx, Philips Medical Systems Lumify™ handheld ultrasound system, Siemens ACUSON™ Sequoia, Esaote MyLabEight™. For the purposes of the following exemplary description, we assume that the images are cines, each of which comprises a set of sequentially time ordered frames. A typical cine set may comprise 40-120 frames saved in a DICOM format.

The method may be implemented on a computer or set of computers having associated processors, memories, display means etc. Alternatively the method may be implemented on a server such as a cloud based server.

A semi- or fully automated network-based procedure for calculating measurements to characterize the type and severity of changes in one or more structures of a human (or animal) heart, and taking as input multiple cines saved (separately) in a DICOM format, will now be described. The procedure makes use of a number of stages as follows, and is further illustrated in the flow diagram of FIG. 1.

Figure 1:
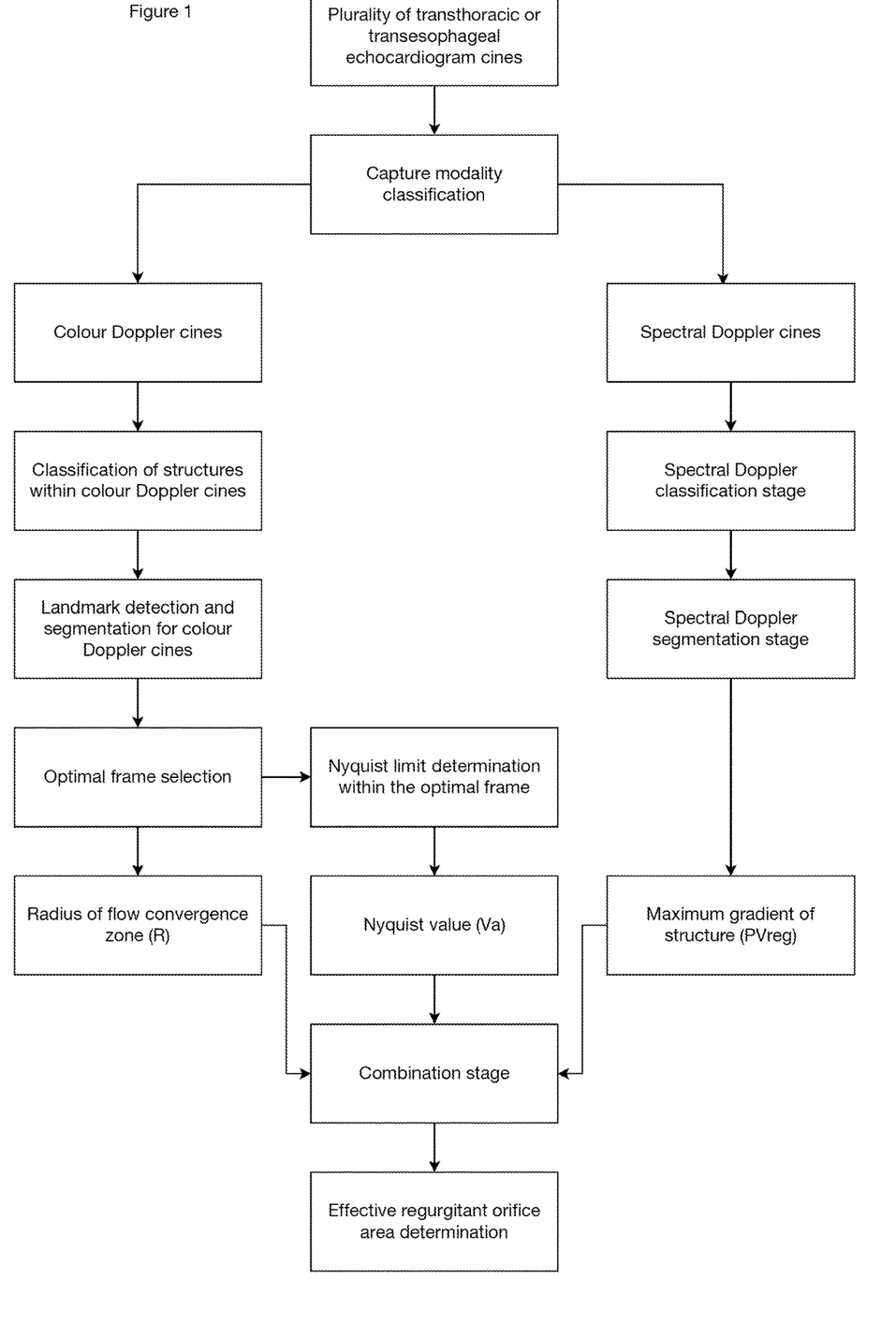
FIG. 1 is a flow diagram illustrating a computer-implemented method for analysing a structure within a patient's heart performed by a software component executing on at least one processor.

1. Capture Modality Classification

A plurality of echocardiogram cines in DICOM format are received as an initial input, with each cine comprising a time ordered sequence of frames. This first classification stage aims to determine, for each cine, the capture modality of the cine.

For each cine the following steps are performed.

(1a) Image pixel data is extracted from the cine. Typically, pixel data comprises multiple arrays of two or more dimensions containing the values for individual pixel intensities ranging from zero to 255. Importantly, no metadata from the received DICOM files is used in this classification stage, which offers an improvement upon known procedures, as use of such metadata might introduce errors due to incorrectly encoded or recorded metadata.

(1b) Pixel data for the first frame in the cine is selected.

(1c) The selected pixel data is provided to a first classification neural network. This is a MobileNet based neural network trained using multiclass classification objective and cross-entropy loss. [MobileNet is a class of Convolutional Neural Networks (CNN) open-sourced by GOOGLE™.] The neural network takes the input pixel data, resizes it into input resolution, converts it into a tensor and passes it through the neural network layers. [Resizing refers to scaling images from one resolution into another using a method such as nearest-neighbour interpolation (for example, converting an image with a height and width of 700 by 500 pixels into 224 by 244 pixels).] The output of the model is a tensor with probabilities for the assessed frame for each of the following categories: B-mode, M-mode, colour Doppler, spectral Doppler and "other".

Steps (1a) to (1c) are repeated for each frame of the cine being assessed in order to generate an output tensor for each frame. Based on an analysis of the probability tensors for all of the frames of the assessed cine (e.g. majority voting), an overall classification is given to the cine, i.e. B-mode, M-mode, colour Doppler, spectral Doppler and "other".

By repeating this for each of the input cines, a capture modality is determined for each cine, without the need to analyse metadata in the respective DICOM format files. [NB. In the following procedures only the colour Doppler and spectral Doppler cines are analysed further, although cines of other modalities may additionally be analysed.]

Figure 2:
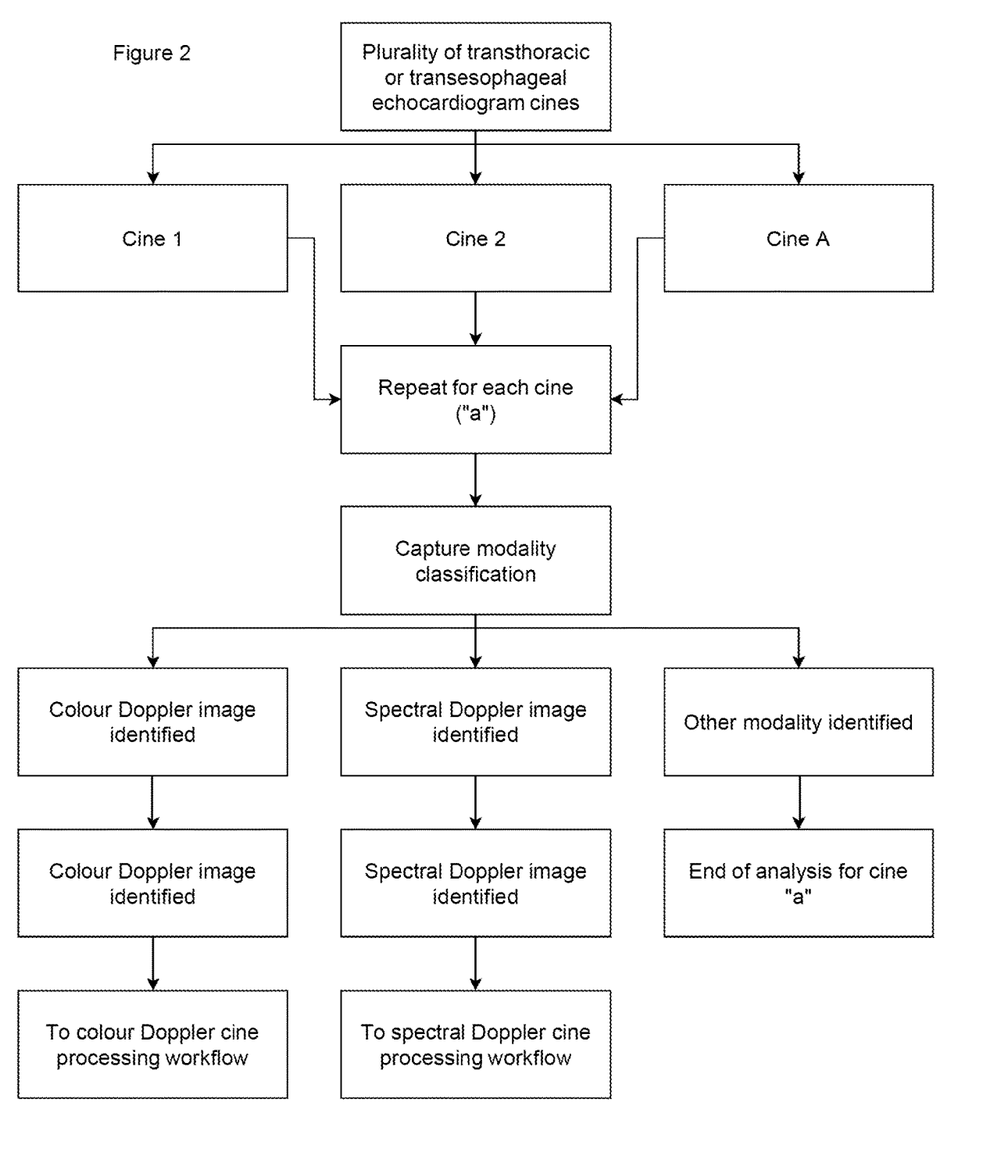
FIG. 2 is a flow diagram illustrating selection of colour Doppler and spectral Doppler cines within the method of FIG. 1.

2. Classification of Structures within Colour Doppler Cines

Those cines identified as colour Doppler modality cines by the first classification stage are selected. For each selected identified cine, pixel data for up to five equally distributed frames is extracted and the following steps performed. Of course, five is only presented here as an exemplary number and more or less of the frames may be used.

(2a) The extracted pixel data is passed into a Colour Doppler classification neural network, frame-by-frame (for the five frames selected). This network is again a MobileNet based neural network trained using multiclass classification objective and cross-entropy loss. The neural network resizes the input (frame) data into input resolution, converts it into a tensor and passes the tensor through the neural network layers. The output of the network is, for each frame of the cine being assessed, a tensor with probabilities for one of the following categories: aortic valve, mitral valve, pulmonary valve, tricuspid valve, interventricular septum, interatrial septum and "other". In other words, the network provides a probability for the presence of each of these structures in a given frame of the cine.

(2b) The cine being assessed is associated with a structure based on the most likely structure as indicated by the set of tensors for the selected frames of the cine (e.g. majority voting).

By repeating this procedure for each of the cines (previously identified as having being captured with the Colour Doppler modality), all of the cines are associated with a structure (aortic valve, mitral valve, etc.). The cines are then grouped according to the structure with which they are associated. Each group may contain zero, one, or more cines.

Figure 3:
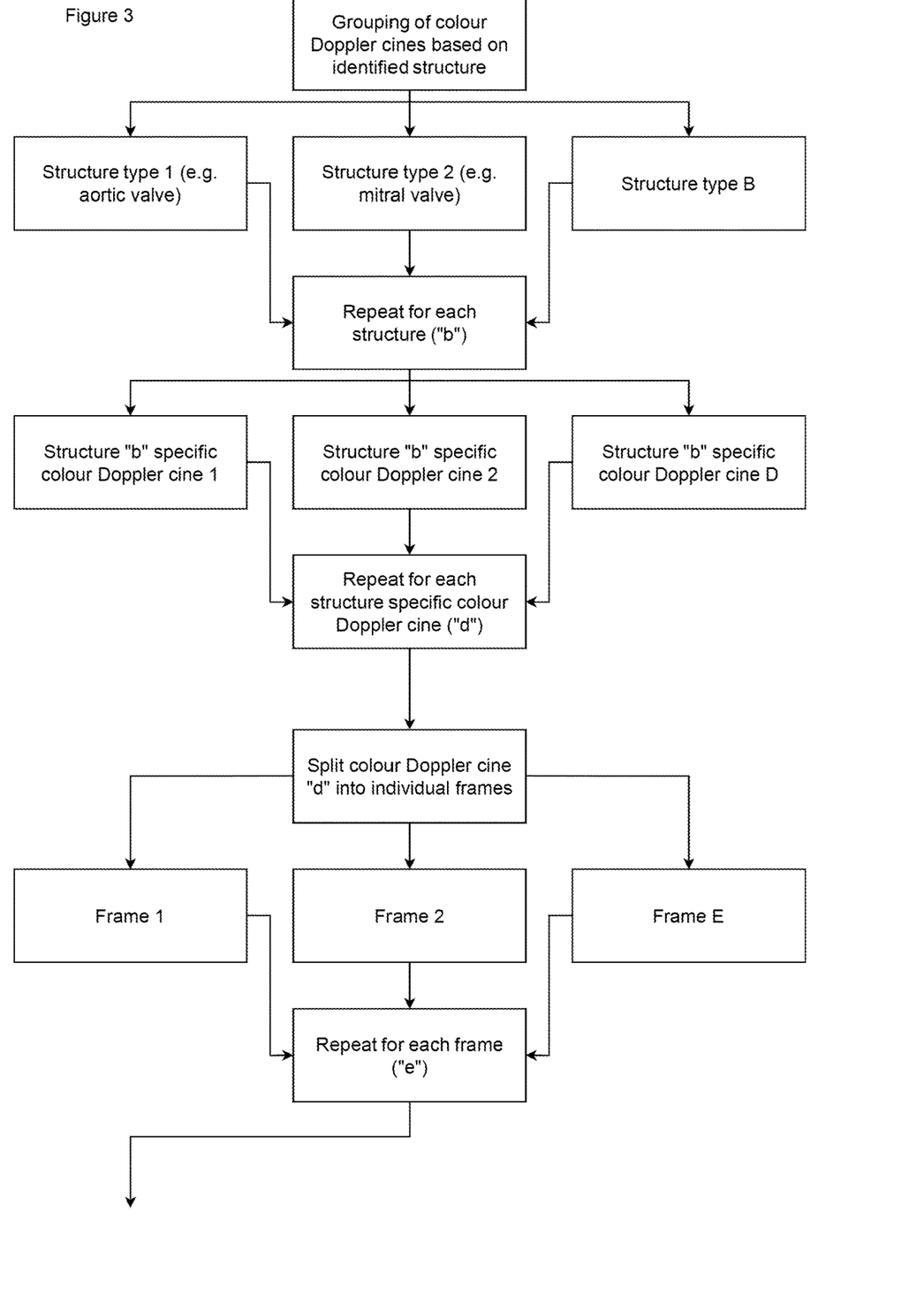
FIG. 3 is a flow diagram illustrating processing of colour Doppler cines and extraction of Radius of flow convergence zone and Nyquist value within the method of FIG. 1.

3. Landmark Detection and Segmentation for Colour Doppler Cines

Each of the groups of cines (excluding any groups with zero cines and the group associated with "other") is then separately analysed. For each cine of the group being analysed the following procedure is carried out.

(3a) Pixel data is extracted from the cine and associated with respective individual frames of the cine.

(3b) Pixel data associated with each frame of the cine is then passed into a colour Doppler instance segmentation and landmark detection neural network. This is a transformer based neural network trained using multiple objectives:
   a) localizing individual jet streams using bounding boxes;
   b) detecting pixels belonging to the localized jet streams;
   c) localizing individual flow convergence zones using bounding boxes;
   d) detecting pixels belonging to the localized flow convergence zones;
   e) detecting locations of vena *contracta* and radius of the flow convergence zone in the localized flow convergence zones.

The neural network resizes the input data into input resolution, converts it into a tensor and passes the tensor through the neural network layers. The neural network then generates an output tensor for the frame under consideration dependent upon the above training objectives. This will, for example, indicate the presence in the frame of zero or more jet streams, zero or more flow convergence zones, the location of vena *contracta* and the flow convergence radius. For the purposes of implementing the neural network, a maximum number of jet streams, flow convergence zones, vena *contracta* and flow convergence radii is defined for each. In this example the limit for each is set to three. The output tensor is resized into the same resolution as the original frame.

The neural network can detect a maximum of three jet streams. If no jet streams are detected, the value for each of the possible three jet streams is set to zero. If one or more jet streams are detected, for each detected jet stream values in the output tensor are processed further. Each position in the output tensor corresponds to a pixel in the original frame and has an assigned value. If a position has a value higher than or equal to 0.5, the pixel is assigned to the jet stream boundary. The number of positions having a value of 0.5 or higher (those considered to constitute an individual jet stream) are counted. The resulting count is then multiplied by physical delta x and physical delta y values (for the two frame directions) to obtain the total area of each jet stream. Thus, for example, if delta x is 0.2 mm and delta y is 0.4 and the number of pixels is 50, the jet stream area corresponds to 50*0.2*0.4=4 mm^2.

In the same way, if no flow convergence zones are detected, the area value for each convergence zone is set to zero. If one or more convergence zones are detected, for each detected convergence zone, the number of positions with values of 0.5 or higher are summed up and multiplied by physical delta x and physical delta y values to obtain the physical dimensions of the convergence zone.

The length of vena *contracta* is extracted from the output tensor and converted into physical units.

Repeating the process (3a) and (3b) for each frame of the assessed cine produces for each cine a tensor containing the described data. Corresponding data can be extracted from the frame tensors and assembled into lists. For example, a list [0, 0, 45, 64, 22] identifies, for a given cine, the sizes—in terms of a number of pixels—of the flow convergence zones detected in five frames of the cine. This indicates that no convergence zone was detected in either the first or the second frames, with a convergence zone detected starting from the third frame. The largest convergence in the example is at frame number four; thus that frame is marked as a frame of interest.

If a given structure group has more than one cine associated with it, the process of extracting flow convergence zone areas for each frame is repeated for each cine of the group and the final frame of interest is chosen as the one that has the largest flow convergence zone area across all lists. For example, a given structure group may contain two cines, for which the following lists are generated for flow convergence zone:[0, 0, 45, 64, 22] and [0, 10, 11, 68, 44]. In this case the final frame for further analysis would be the fourth frame in the second cine and the corresponding area would be 68.

NB. If no jet area and vena *contracta* size are determined within a selected frame, i.e. the area or size of either is determined to be zero, the frame is discarded and the frame of interest is chosen as the frame with the next highest value for flow convergence zone area (in the above example this would be the fourth frame in the first cine). This is repeated as necessary until an optimal frame for further analysis is identified. The radius of the flow convergence zone within the optimal frame is converted into physical dimensions.

4. Nyquist Limit Determination within the Optimal Frame

An important parameter when analysing colour Doppler cines is the Nyquist limit which defines the maximum flow rate that is visible within the cine. This is usually presented within the pixel data of a frame and conventionally is read visually by an operator. It is proposed here to implement a neural network based procedure for determining the Nyquist value from the identified optimal frame.

To achieve this, the optimal frame is passed into a Nyquist limit object detection neural network that detects the region of the frame containing the Nyquist limit value. This is a transformer based neural network trained using localization loss. The neural network resizes the frame into an input resolution, converts it to a tensor and passes the tensor through the neural network layers. The neural network then detects the location of the Nyquist limit value within the frame and produces an output tensor with its location. The output tensor is resized into the same resolution as the original frame. The Nyquist limit value is then extracted from its location in the original frame using optical character recognition.

Overall, the following values are produced for each structure in the optimal frame when possible: a) Nyquist limit value; b) one or more vena *contracta* lengths; c) one or more flow convergence zone radii; d) one or more jet areas; e) one or more flow convergence zone areas.

Figure 4:
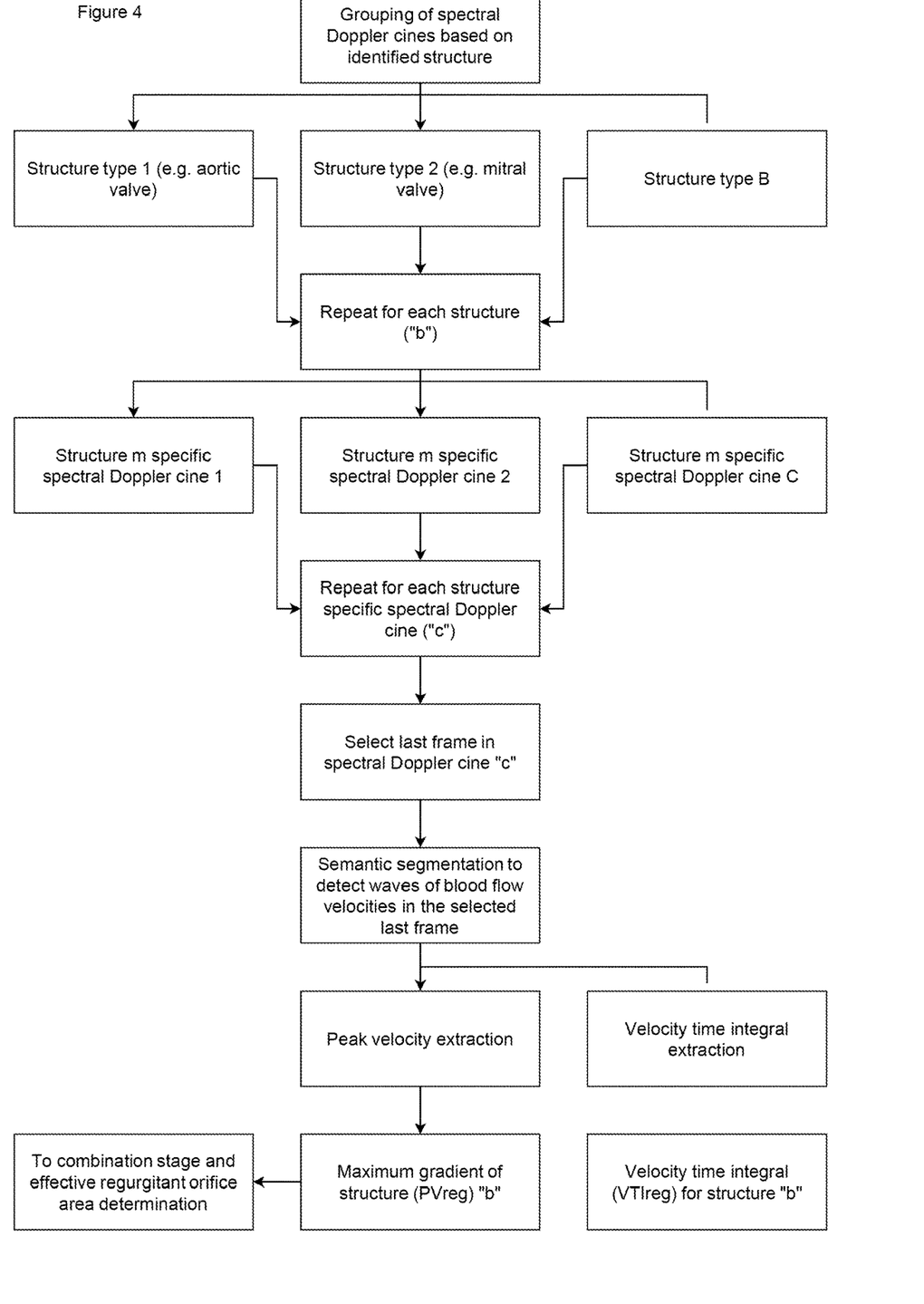
FIG. 4 is a flow diagram illustrating processing of spectral Doppler cines and extraction of Maximum gradient of structure within the method of FIG. 1.

5. Spectral Doppler Classification Stage

Those cines identified as spectral Doppler modality cines by the first classification stage are selected. For each selected cine, the last frame is extracted.

(5a) Pixel data for the last frame is passed into a spectral Doppler classification neural network to determine the observed structure. This is again a MobileNet based neural network trained using multiclass classification objective and cross-entropy loss. The neural network resizes the pixel data into an input resolution, converts it into a tensor and passes the tensor through the neural network layers. The output of the model is a tensor with probabilities for each of the following categories: aortic valve, mitral valve, pulmonary valve, tricuspid valve, interventricular septum and interatrial septum and "other".

(5b) The cine being assessed is associated with a structure based on the most likely structure as indicated by the generated tensor (for the final frame of the cine).

By repeating this procedure for each of the cines (previously identified as having being captured with the Spectral Doppler modality), each cine is further associated with a structure (aortic valve, mitral valve, etc.). The cines are then grouped according to the structure with which they are associated. Each group may contain zero, one, or more cines.

5. Spectral Doppler Segmentation Stage

Each of the groups of cines (excluding any groups with zero cines and the group associated with "other") is then separately analysed. For each cine of the group being analysed the following procedure is carried out.

(6a) Pixel data is extracted from the cine and associated with respective individual frames of the cine. Data for the last frame of the cine is selected.

(6b) Pixel data for the selected last frame is passed into a Spectral Doppler segmentation neural network. This is a transformer based neural network trained using semantic segmentation objective and Dice loss. Semantic segmentation in computer vision refers to assigning a given category (such as jet stream, flow convergence zone, background and others) to each pixel in the input image. Dice loss is calculated using the formula: $1-2*[(Ytrue \cup Ypred)/(Ytrue+Ypred)]$ where Ytrue and Ypred are the pixel-wise masks of the ground truth and predicted object, respectively. The neural network resizes the input data into input resolution, converts it into a tensor and passes it through the neural network layers. The neural network then detects zero or more waves of blood flow velocities.

(6c) The output tensor is resized into the same resolution as the original frame.

(6d) Individual blood flow velocity waves are extracted from outputs. Blood flow velocity wave peaks and areas correspond to peak velocity and velocity time integrals respectively, and are extracted for further analysis.

(6e) Peak velocity (PVreg–maximum regurgitant gradient of structure) and velocity time integrals (VTIreg–velocity time integral regurgitation) are converted into physical units.

For a given group of cines, the maximum values for PVreg and VTIreg are selected and identified as the values for the group. The result of repeating this procedure for each of the groups of cines are values of PVreg and VTIreg for each of the assessed structures, i.e. aortic valve, mitral valve etc.

7. Combination Stage

We now have, for each of the colour Doppler and spectral Doppler modalities, data for each assessed structure, namely a) Nyquist limit value; b) one or more vena *contracta* lengths; c) one or more flow convergence zone radii; d) one or more flow convergence zone areas for the colour Doplar modality, and PVreg and VTIreg for the spectral Doppler modality. The Effective regurgitant orifice area (EROA) and Regurgitant Volume are then calculated for each structure, i.e. aortic valve, the mitral valve etc, as follows:

(7a) Effective regurgitant orifice area (EROA) is then calculated using the following formula: $(2*\pi*R**2\pi Va)/PVreg$, where  i. R—radius of flow convergence zone
 ii. Va—Nyquist limit
 iii. PVreg—maximum gradient of structure (7b) Regurgitant Volume is calculated using the formula: EROA*VTIreg  i. VTIreg—velocity time integral regurgitation (7c) EROA and regurgitant volume are metrics used in the quantitative analysis of valvular insufficiency. The following publications provide examples of the use of this data to provide diagnosis and treatment recommendations.

https://academic.oup.com/view-large/41542917
Mitral regurgitation (MR):
 Mild MR: EROA (mm2) <20 and regurgitant volume (mL) <30.
 Mild-to-moderate MR: EROA (mm2) 20-29 and regurgitant volume (mL) 30-44.
 Moderate-to-severe MR: EROA (mm2) 30-39 and regurgitant volume (mL) 45-59.
 Severe MR: EROA (mm2) ≥40 and regurgitant volume (mL)
Treatment of severe mitral regurgitation requires surgical intervention.
https://academic.oup.com/view-large/41542736
Aortic regurgitation (AR):
 Mild AR: EROA (mm2) <10 and regurgitant volume (mL) <30.
 Mild-to-moderate AR: EROA (mm2) 10-19 and regurgitant volume (mL) 30-44.
 Moderate-to-severe AR: EROA (mm2) 20-29 and regurgitant volume (mL) 45-59.
 Severe AR: EROA (mm2) ≥30 and regurgitant volume (mL)
https://academic.oup.com/view-large/41542967
Tricuspid regurgitation (TR):
 Severe TR: EROA (mm2) ≥40 and regurgitant volume (mL)
 Mild and moderate cut-off values are undefined.
https://academic.oup.com/view-large/41542819
Pulmonary regurgitation (PR) cut-off values are undefined.

(7d) Vena *contracta* is a metric used in the semi-quantitative analysis of valvular insufficiency.
https://academic.oup.com/view-large/41542917
Mitral regurgitation (MR):
 Mild MR: vena *contracta* (mm) <3.
 Moderate MR: vena *contracta* (mm) 4-6.
 Severe MR: vena *contracta* (mm) ≥7.
https://academic.oup.com/view-large/41542736
Aortic regurgitation (AR):
 Mild AR: vena *contracta* (mm) <3.
 Moderate AR: vena *contracta* (mm) 4-5.
 Severe AR: vena *contracta* (mm) ≥6.
https://academic.oup.com/view-large/41542967
Tricuspid regurgitation (TR):
 Mild TR cut-off values are undefined.
 Moderate TR: vena *contracta* (mm) <7.
 Severe TR: vena *contracta* (mm) ≥7.
https://academic.oup.com/view-large/41542819
Pulmonary regurgitation (PR) cut-off values are undefined.

The following table provides further information relating to the various neural networks identified above:

| Neural network | Architecture | Number of frames in training dataset | Input resolution (height, width) | Objective | Loss function |
|---|---|---|---|---|---|
| First classification neural network | MobileNet | 120 000 | 64, 64 | Multiclass classification | Cross-entropy loss |
| Colour Doppler classification neural network | MobileNet | 40 000 | 128, 128 | Multiclass classification | Cross-entropy loss |
| Spectral Doppler classification neural network | MobileNet | 40 000 | 128, 128 | Multiclass classification | Cross-entropy loss |
| Spectral Doppler segmentation neural network | Transformer based architecture | 10 000 | 192, 256 | Semantic segmentation | Dice loss |
| Colour Doppler instance segmentation and landmark detection neural network | Transformer based architecture | 10 000 | 192, 256 | Instance segmentation and landmark detection | Localization loss, Dice loss, Mean squared error loss |
| Nyquist limit object detection neural network | Transformer based architecture | 8 000 | 192, 256 | Object detection | Localization loss |

The invention claimed is:

1. A computer-implemented method of analysing a structure within a patient's heart performed by a software component executing on at least one processor, comprising the steps of:
   receiving from a memory, a patient study comprising a plurality of transthoracic echocardiography and/or transesophageal echocardiography images of the patient's heart obtained by an ultrasound device;
   extracting respective sets of pixel data from the transthoracic echocardiography and/or transesophageal echocardiography images;
   using one or more trained machine learning algorithms to analyse the sets of pixel data to
   a) identify first transthoracic echocardiography and/or transesophageal echocardiography images captured using a colour Doppler modality and assign one or more of the first transthoracic echocardiography and/or transesophageal echocardiography images to the structure,
   b) identify second transthoracic echocardiography and/or transesophageal echocardiography images captured using spectral Doppler modality and assign one or more of the second transthoracic echocardiography and/or transesophageal echocardiography images to the structure,
   c) determine a flow convergence zone radius R from an analysis of the first transthoracic echocardiography and/or transesophageal echocardiography images assigned to the structure; and
   d) determine a maximum gradient of structure, PVreg, from an analysis of the second transthoracic echocardiography and/or transesophageal echocardiography images assigned to the structure; and
   combining the flow convergence zone radius, R, the maximum gradient of structure PVreg, and a Nyquist value Va identified for the colour Doppler modality, to determine an Effective Regurgitant Orifice Area, EROA for the structure according to the formula:

$$(2*\pi*R^{**}2 \times Va)/\text{PVreg}.$$

2. The computer-implemented method according to claim 1, further comprising
   using said one or more trained neural networks to determine a velocity time integral regurgitation, VTIreg, from an analysis of the second transthoracic echocardiography and/or transesophageal echocardiography images assigned to the structure,
   combining the EROA and the VTIreg to determine a Regurgitant Volume for the structure.

3. The computer-implemented method according to claim 2, wherein the Regurgitant Volume is determined using the formula:

$$\text{EROA} * \text{VTIreg}.$$

4. The computer-implemented method according to claim 1, further comprising using the one or more trained machine learning algorithms to determine a location of said Nyquist value within the first transthoracic echocardiography and/or transesophageal echocardiography images assigned to the structure, and applying optical character recognition to the location to determine the Nyquist value.

5. The computer-implemented method according to claim 1, wherein the plurality of transthoracic echocardiography and/or transesophageal echocardiography images are cines and each of the cines comprises a plurality of frames.

6. The computer-implemented method according to claim 5, wherein, for one or each of steps a) and b), said assignment of the one or more of the first transthoracic echocardiography and/or transesophageal echocardiography and the second transthoracic echocardiography and/or transesophageal echocardiography images to the structure comprises using a trained classification neural network to separately analyse a plurality of frames of a respective image for the presence of the structure and combining outputs for the analysed frames to allocate the respective image to the structure.

7. The computer-implemented method according to claim 5, wherein, for one or each of steps c) and d), a segmentation and landmark detection neural network is used to identify a single frame of the one or more of the first transthoracic echocardiography and/or transesophageal echocardiography and the second transthoracic echocardiography and/or transesophageal echocardiography images assigned to the structure and having the largest flow convergence zone radius R and/or maximum gradient of structure, PVreg.

8. The computer-implemented method according to claim 1, wherein the plurality of transthoracic echocardiography and/or transesophageal echocardiography images are still images.

9. The computer-implemented method according to claim 1, each of the transthoracic echocardiography and/or transesophageal echocardiography images being received from said memory as a DICOM format file.

10. The computer-implemented method according to claim 1, said structure being one of an aortic valve, mitral valve, pulmonary valve, tricuspid valve, interventricular septum, or interatrial septum.

11. A method of diagnosing cardiovascular disease comprising performing the computer-implemented method of claim 1 to determine the EROA for the structure of a heart.

* * * * *